United States Patent
Barker et al.

(10) Patent No.: US 9,173,398 B2
(45) Date of Patent: Nov. 3, 2015

(54) BIOCIDE COMPOSITIONS

(75) Inventors: Phyllis Barker, West Harrison, IN (US); Alefesh Hailu, Cincinnati, OH (US)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/539,794

(22) Filed: Jul. 2, 2012

(65) Prior Publication Data
US 2013/0012391 A1 Jan. 10, 2013

Related U.S. Application Data

(60) Provisional application No. 61/504,504, filed on Jul. 5, 2011.

(51) Int. Cl.
*A01N 43/56* (2006.01)
*A01P 13/00* (2006.01)

(52) U.S. Cl.
CPC ...................................... *A01N 43/56* (2013.01)

(58) Field of Classification Search
CPC ..... A01N 43/44; A01N 43/713; A01N 47/38; A01N 43/56; A01N 2300/00; A01N 25/02; C07D 205/04
See application file for complete search history.

(56) References Cited

U.S. PATENT DOCUMENTS

| | | | |
|---|---|---|---|
| 3,709,676 A * | 1/1973 | Vartiak | 504/243 |
| 2004/0266623 A1 * | 12/2004 | Armbruster et al. | 504/130 |
| 2006/0063676 A1 * | 3/2006 | Brigance et al. | 504/116.1 |

FOREIGN PATENT DOCUMENTS

| | | |
|---|---|---|
| EP | 2147599 | 1/2010 |
| WO | WO 2007/140332 | 12/2007 |

OTHER PUBLICATIONS

ScienceLab.com Chemicals & Laboratory Equipment, "2,4-Dichlorophenoxyacetic acid MSDS", created: Oct. 9, 2005.*
International Search Report in PCT/EP2012/062949 mailed Jul. 23, 2013, 3 pages.

* cited by examiner

*Primary Examiner* — Johann R Richter
*Assistant Examiner* — Genevieve S Alley
(74) *Attorney, Agent, or Firm* — Servilla Whitney LLC

(57) ABSTRACT

Described is a biocide composition, comprising: a herbicide; a fatty acid amide; a fatty acid; and optionally an emulsifier and/or a polyol. The composition exhibits an improved stability, especially at lower temperatures, and is both environmentally friendly and non-toxic.

23 Claims, No Drawings

BIOCIDE COMPOSITIONS

CROSS-REFERENCE TO RELATED APPLICATIONS

This application claims priority under 35 U.S.C. §119(e) to U.S. Provisional Application No. 61/504,504, filed Jul. 5, 2011, the disclosure of which is incorporated herein by reference in its entirety.

TECHNICAL FIELD

The present invention relates to the area of agrochemicals and, specifically, to emulsifiable concentrates for herbicides comprising an environmentally friendly and non-toxic blend of solvents.

BACKGROUND

It is a known drawback of many herbicides that they are solids and show poor solubility in water and other solvents, leading to difficulty producing concentrates with sufficient amounts of active matter. Typically, aromatic hydrocarbons are used as solvents, but, although they show high solvent power, they are considered to be carcinogenic, unfriendly to the environment, and exhibit an unpleasant odor. In the past, they were replaced, at least in part, by oleochemicals showing a higher degree of biodegradability. Methyl esters of fatty acids were used, although their solvent power is lower than, for example, NMP or other aromatics. As a matter of fact, methyl esters do not prevent the separation of crystals out of the solution once the temperatures go down to 5° C. or lower.

Accordingly, provided are emulsifiable concentrates comprising up to 5% b.w. herbicides, in particular solids, as, for example, pyraflufen, showing a better solubility in particular at lower temperatures in order to prevent separation and crystallization. In addition, the concentrates exhibit a more pleasant odor and are based on solvents which are non-toxic, highly biodegradable, and environmentally friendly.

SUMMARY

Embodiments of the present invention are directed to a biocide composition comprising a herbicide, a fatty acid amide, a fatty acid, and, optionally, an emulsifier and/or a polyol.

In one or more embodiments, the herbicide is a solid. The herbicide can exhibit solubility in water of less that 5 g/L at a temperature of 20° C. and a water hardness of at most 1000 ppm.

In a specific embodiment, the herbicide is pyraflufen-ethyl.

In one or more embodiments, the fatty acid amide is according to general formula (I), $R^1CONR^2R^3$ (I), wherein $R^1CO$ represents a linear or branched, saturated or unsaturated, optionally hydroxyl-substituted acyl radical having 2 to 22 carbon atoms and 0 or 1 to 3 double bonds, and $R^2$ and $R^3$ independently represent either hydrogen or alkyl radicals having 1 to 12 carbon atoms.

In one or more embodiments, the fatty acid amide is derived from a fatty acid having 6 to 10 carbon atoms or lactic acid. The fatty acid amide can be a fatty acid dialkyl amide.

In a specific embodiment, the fatty acid amide is a fatty acid dimethyl amide. In one or more embodiments, the fatty acid amide is a $C_6$-$C_{10}$ fatty acid dimethyl amide.

In one or more embodiments, the fatty acid is according to general formula (II), $R^1CO$—OH (II), wherein $R^2CO$ represents a linear or branched, saturated or unsaturated, optionally hydroxyl-substituted acyl radical having 6 to 22 carbon atoms and 0 or 1 to 3 double bonds.

In one or more embodiments, the fatty acid is a C16-C18 fatty acid having 0 or 1 to 3 double bonds. In a specific embodiment, the fatty acid is tall oil fatty acid.

In one or more embodiments, the emulsifier is a non-ionic emulsifier. The emulsifier can be a polymeric non-ionic emulsifier.

In one or more embodiments, the emulsifier is the alkoxylation product of an alkyl phenol. In a specific embodiment, the emulsifier is a nonyl phenol EO/PO block copolymer.

In one or more embodiments, the polyol is selected from the group consisting of glycerol, alkylene glycols, technical oligoglycerol mixtures with a degree of self-condensation of 1.5 to 10, methylol compounds; lower alkyl glucosides, sugar alcohols containing 5 to 12 carbon atoms, sugars containing 5 to 12 carbon atoms, and amino sugars.

In one or more embodiments, the biocide composition comprises a solid herbicide, a fatty acid amide derived from a $C_6$-$C_{10}$ fatty acid or lactic acid, a $C_{16}$-$C_{18}$ fatty acid, and, optionally, a non-ionic emulsifier and/or a polyol.

In one or more embodiments, the biocide composition comprises about 0.1 to about 5% b.w. a herbicide, about 50 to about 90% b.w. a fatty acid amide, about 5 to about 15% b.w a fatty acid, and, optionally, about 0.5 to about 5% b.w. an emulsifier and/or about 0.1 to about 1% b.w. a polyol, with the proviso that the amounts add to 100%.

In one or more embodiments, the biocide composition comprises about 0.1 to about 5% b.w. pyraflufen-ethyl, about 50 to about 90% b.w. a $C_6$-$C_{10}$ fatty acid dimethyl amide, about 5 to about 15% b.w. tall oil fatty acid, and, optionally, about 0.5 to about 5% b.w. nonyl phenol EO/PO block copolymer and/or about 0.1 to about 1% b.w. propylene glycol, with the proviso that the amounts add to 100%.

A second aspect of the present invention is directed to a method of controlling weeds, the method comprising using the composition according to the invention as a weed control agent.

A further aspect of the present invention is directed to a method of protecting crops, the method comprising using the composition according to the invention as a crop protection agent.

A still further aspect of the present invention is directed to a process for controlling and fighting weed growth in a crop field, wherein a composition according to the invention is diluted with water to provide a sprayable emulsion or dispersion and said emulsion or dispersion is applied to the crop. In one or more embodiments, the emulsion or dispersion is in the form of a tank mix having a water content of 50 to 95% b.w.

DETAILED DESCRIPTION

Before describing several exemplary, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

Provided are biocide compositions, comprising:
(a) Herbicides;
(b) Fatty acid amides;
(c) Fatty acids; and optionally
(d) Emulsifiers and/or
(e) Polyols.

Surprisingly, it has been observed that using a blend of fatty acid amides and fatty acids, also solid herbicides like pyraflufen, which typically show a very poor solubility in water and other solvents, can be easily formulated. The concentrates remain stable even when cooled down to temperatures between +5 and −5° C. independently from water hardness, what typically has also had a disadvantageous impact on solubility. In addition, the solvent blends comply with the regulations as set out in the 40 CFR 180 listing. Also, the formulations are free of naphthalene and show higher flash points.

Finally, the solvent blends are fully biodegradable, non-toxic, and environmentally friendly. Stability can be further improved by adding emulsifiers, in particular non-ionic polymers, and small amounts of polyols, in particular glycols.

Herbicides

A herbicide (Compound a) is a pesticide used to kill unwanted plants. Selective herbicides kill specific targets while leaving the desired crop relatively unharmed. Some of these act by interfering with the growth of the weed and are often based on plant hormones. Herbicides used to clear waste ground are non-selective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In general, active ingredients representing including various chemical classes and corresponding examples can be used Anilides such as propanil Aryloxycarboxylic acids e.g. MCPA-thioethyl Aryloxyphenoxypropionates e.g. clodinafop-propargyl, cyhalofop-butyl, diclofops, fluazifops, haloxyfops, quizalofops, Chloroacetamides e.g. acetolochlor, alachlor, butachlor, dimethenamid, metolachlor, propachlor Cyclohexanedione oximes e.g. clethodim, sethoxydim, tralkoxydim, Benzamides such as isoxaben Benzimidazoles such as dicamba, ethofumesate Dinitroanilines e.g. trifluralin, pendimethalin, Diphenyl ethers e.g. aclonifen, oxyfluorfen, The glycine derivative glyphosate, a systemic nonselective (it kills any type of plant) herbicide used in no-till burndown and for weed control in crops that are genetically modified to resist its effects, Hydroxybenzonitriles e.g. bromoxynil, Imidazolinones e.g. fenamidone, imazapic, imazamox, imazapic, imazapyr, imazaquin, Isoxazolidinones e.g. clomazone Paraquat as bypyridylium, Phenyl carbamates e.g. desmedipham, phenmedipham, Phenylpyrazoles e.g. pyraflufen-ethyl Phenylpyrazolines e.g. pinoxaden, Pyridinecarboxylic acids or synthetic auxins e.g. picloram, clopyralid, and triclopyr, Pyrimidinyloxybenzoics e.g. bispyrtbac-sodium Sulfonylureas e.g. amidosulfuron, azimsulfuron, bensulfuron-methyl, chlorsulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron, Triazolopyrimidines e.g. penoxsulam, metosulam, florasulam, Triketones e.g. mesotriones, sulcotrione, Ureas e.g. diuron, linuron, Phenoxycarboxylic acids such as 2,4-D, MCPA, MCPB, mecoprops, Triazines such as atrazine, simazine, terbuthylazine, and mixtures thereof. In one or more embodiments, the herbicides are those which are solid at 20° C. and exhibit solubility in water of less than 5 g/l at a temperature of 20° C. and a water hardness of at most 1000 ppm, for example pyraflufens, and in particular pyraflufen-ethyl.

Fatty Acid Amides

Fatty acid amides (Compound b) typically follow general formula (I)

$$R^1CONR^2R^3 \quad (I)$$

wherein $R^1CO$ represents a linear or branched, saturated or unsaturated, optionally hydroxyl-substituted acyl radical having 2 to 22 carbon atoms and 0 or 1 to 3 double bonds, and $R^2$ and $R^3$ independently represent either hydrogen or alkyl radicals having 1 to 12 carbon atoms. Typical examples are amides derived from capronic acid, caprylic acid, capric acid, lauric acid, myrystic acid, palmitic acid, stearic acid, isostearic acid, 12-hydroxy stearic acid, ricinoleic acid, oleic acid, linoleic acid, linolenic acid, gadoleic acid, arachidonic acid, erucic acid, behenic acid and mixtures thereof. Also suitable are amides derived from hydroxy acids, for example citric acid, or, in particular, lactic acid. Indeed, in one or more embodiments, the amides are derived from either fatty acids having 6 to 10 carbon atoms or lactic acid.

In a specific embodiment the fatty acid amides represent fatty acid dialkyl amides, in particular fatty acid dimethyl amides. Overall preferred are $C_6$-$C_{10}$ fatty acid dimethyl amides, as for example Agnique® KE 3658 (Cognis GmbH).

The fatty acid amides represent the major part of the solvent blend and can be present in the composition in amounts of from about 50 to about 90, and in particular from about 75 to about 85% b.w.

Fatty Acids

Suitable fatty acids (Compound c) follow general formula (II)

$$R^2CO-OH \quad (II)$$

wherein $R^2CO$ represents for a linear or branched, saturated or unsaturated, optionally hydroxyl-substituted acyl radical having 6 to 22 carbon atoms and 0 or 1 to 3 double bonds. Typical examples are capronic acid, caprylic acid, capric acid, lauric acid, myrystic acid, palmitic acid, stearic acid, isostearic acid, 12-hydroxy stearic acid, ricinoleic acid, oleic acid, linoleic acid, linolenic acid, gadoleic acid, arachidonic acid, erucic acid, behenic acid and mixtures thereof. Instead of the free acids, salts are also applicable, for example sodium, potassium, lithium, ammonium and alkanolammonium salts, especially in those cases where the herbicide is also a salt. In one or more embodiments, the fatty acid component is a $C_{16}$-$C_{18}$ fatty acids having 0 and/or 1 to 3 double bonds, in particular tall oil fatty acid. The fatty acids can be present in the formulation in amounts of from about 5 to about 15, and preferably from about 7 to about 12% b.w.

Emulsifiers

It has been found advantageous to improve stability at temperatures below 0° C. by adding emulsifiers (Compound D), in particular non-ionic emulsifiers including, for example:

products of the addition of 2 to 50 mol ethylene oxide and/or 0 to 50 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, and The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The emulsifiers according to one or more embodiments are described in more detail as follows:

a) Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30, and preferably 5 to 10, mol ethylene oxide onto the partial glycerides mentioned are also suitable.

b) Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30, and preferably 5 to 10, mol ethylene oxide onto the sorbitan esters mentioned are also suitable.

c) Alk(en)yl Oligoglycosides

The alkyl or alkenyl oligoglycosides representing emulsifiers according to one or more embodiments may be derived from aldoses or ketoses containing 5 or 6 carbon atoms, preferably glucose. Accordingly, the preferred alkyl and/or alkenyl oligoglycosides are alkyl or alkenyl oligoglucosides. These materials are also known generically as "alkyl polyglycosides" (APG). The alk(en)yl oligoglycosides according to the invention correspond to formula (III):

$$R^1O[G]_p \qquad (III)$$

wherein $R^1$ is an alkyl or alkenyl radical having from 6 to 22 carbon atoms, G is a sugar unit having 5 or 6 carbon atoms and p is a number from 1 to 10. The index p in general formula (II) indicates the degree of oligomerisation (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is mostly a broken number. Alk(en)yl oligoglycosides having an average degree of oligomerisation p of 1.1 to 3.0 are preferably used. Alk(en)yl oligoglycosides having a degree of oligomerisation below 1.7 and, more particularly, between 1.2 and 1.4 are preferred from the applicational point of view. The alkyl or alkenyl radical $R^1$ may be derived from primary alcohols containing 4 to 22 and preferably 8 to 16 carbon atoms. Typical examples are butanol, caproic alcohol, caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof such as are formed, for example, in the hydrogenation of technical fatty acid methyl esters or in the hydrogenation of aldehydes from Roelen's oxo synthesis. Alkyl oligoglucosides based on hydrogenated $C_8$-$C_{16}$ coconut oil alcohol having a DP of 1 to 3 are preferred. Also suitable are alkoxylation products of alkyl oligoglucosides, for example adducts of 1 to 10 moles ethylene oxide and/or 1 to 5 moles propylene oxide to $C_8$-$C_{10}$ or $C_{12}$-$C_{18}$ alkyl oligoglucoside having a DP between 1.2 and 1.4.

d) Alkoxylated Vegetable Oils and Copolymers

Suitable emulsifiers are castor oil, rape seed oil, soy bean oil ethoxylated with 3 to 80 moles ethylene oxide (Agnique® CSO 35, Agnique® SBO 10, Agnique® SBO 60). Typical copolymers are ethoxylated and propoxylated block and/or random polymers of $C_2$-$C_{22}$ linear or branched alcohols or alkyl phenols.

In one or more embodiments, the non-ionic emulsifiers represent polymeric alkoxylation products of alkyl phenols, preferably of nonyl phenols. Particularly useful are nonyl phenol EO/PO block copolymers comprising up to 50 ethylene oxide and up to 50 propylene oxide unit, as for example Agnique® BP NP-4030 (Cognis GmbH). In one or more embodiments, the emulsifiers and the fatty acids are used in ratios by weight of about 10:90 to about 40:60, and in particular about 25:75.

Polyols

It has also been found advantageous to add small amounts of polyols (Compound e) in order to further improve solubility and avoid haze formation in the concentrates. Suitable polyols can be selected from the following groups:

glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcohol amines, such as diethanol amine or 2-aminopropane-1,3-diol.

Particularly useful are alkylene glycols, in particular ethylene glycol and preferably propylene glycol which can be added in amounts of from about 0.1 to about 5, and in particular from about 0.5 to about 2% b.w.

Compositions

Further specific embodiments of the invention are directed to specific concentrates, more particularly providing compositions comprising:
(a) Solid herbicides;
(b) Fatty acid amides derived from $C_6$-$C_{10}$ fatty acids or lactic acid;
(c) $C_{16}$-$C_{18}$ fatty acids; and optionally
(d) Non-ionic emulsifiers and/or
(e) Polyols.

And, in one or more embodiments, compositions, comprising
(a) about 0.1 to about 5% b.w. herbicides;
(b) about 50 to about 90% fatty acid amides;
(c) about 5 to about 15% b.w. fatty acids; and optionally
(d) about 0.5 to about 5% b.w. emulsifiers and/or
(e) about 0.1 to about 1% b.w. polyols
on condition that the amounts add to 100%.

In a specific embodiment, the compositions comprise
(a) about 0.1 to about 5% b.w. pyraflufen-ethyl;
(b) about 50 to about 90% $C_6$-$C_{10}$ fatty acid dimethyl amides;
(c) about 5 to about 15% b.w. tall oil fatty acid; and optionally
(d) about 0.5 to about 5% b.w. nonyl phenol EO/PO block copolymer and/or
(e) about 0.1 to about 1% b.w. propylene glycol
on condition that the amounts add to 100%.

INDUSTRIAL APPLICATION

Further embodiments relate to the use of a composition as explained above as a weed control and/or crop protection agent.

The invention also provides for a process for controlling and fighting weed growth in a field, according to which a composition according to the invention is diluted with water to provide a sprayable emulsion or dispersion and said emulsion or dispersion is applied to the crop. Typically, one applies emulsions or dispersions in form of a tank mix having a water content of 50 to 95% b.w.

The invention is now described with reference to the following examples. Before describing several exemplary embodiments of the invention, it is to be understood that the invention is not limited to the details of construction or process steps set forth in the following description. The invention is capable of other embodiments and of being practiced or being carried out in various ways.

EXAMPLES

Example 1 and 2, Comparative Example C1

Solubility of pyraflufen-ethyl in two solvents was evaluated by preparing compositions of 1 to 10% b.w. of the herbicide in various solvents at 20° C. The solutions were cooled down to 0° C. and allowed to thaw three times. The evaluation was done after the last defrosting step. The results are shown in Table 1. (+) means that the herbicide is fully dissolved and the solution is clear, (−) means that the solution is incomplete and/or the solution is hazy. Examples 1 and 2 are according to the invention, Example C1 serves for comparison.

TABLE 1

Solubility of pyraflufen-ethyl

| Ex. | Solvents | \multicolumn{6}{c}{Solubility herbicide [% b.w.]} |
| | | 1.0 | 2.5 | 5.0 | 7.5 | 8.5 | 10.0 |
| --- | --- | --- | --- | --- | --- | --- | --- |
| 1 | $C_6$-$C_{10}$ Fatty acid dimethyl amide | + | + | + | + | + | − |
| 2 | Lactic acid dimethyl amide | + | + | + | + | + | − |
| C1 | $C_6$-$C_{10}$ Fatty acid methyl ester | + | + | − | − | − | − |

Examples 3 to 5, Comparative Examples C2 to C4

Emulsion stability was tested by dissolving 50 ml of some emulsifiable concentrates at 20° C. in 950 ml of water showing different hardness. The samples were stored at 20° C. and stability evaluated over a period from 0.5 to 24 hours. The results are compiled in Table 2. Examples 3 to are according to the invention, Examples C2 to C4 serve for comparison. (+) means that the emulsion is homogenous and clear (#) stands for homogenous, but hazy and (−) for inhomogeneous.

TABLE 2

Emulsion stability (all amounts in % b.w.)

| Compound | 3 | 4 | 5 | C2 | C3 | C4 |
| --- | --- | --- | --- | --- | --- | --- |
| Pyraflufen-ethyl | 2.5 | 2.5 | 2.5 | 2.5 | 2.5 | 2.5 |
| $C_6$-$C_{10}$ Fatty acid dimethyl amide | 82.0 | 82.0 | 82.0 | — | — | — |
| $C_6$-$C_{10}$ Fatty acid methyl ester | — | — | — | 82.0 | 82.0 | 82.0 |
| Tall oil fatty acid | 15.5 | 12.0 | 11.5 | 15.5 | 12.0 | 11.5 |
| Nonyl phenol + 40EO + 30PO | — | 3.5 | 3.5 | — | 3.5 | 3.5 |
| Propylene glycol | — | — | 0.5 | — | — | 0.5 |
| Examples | 3 | 4 | 5 | C2 | C3 | C4 |
| \multicolumn{7}{c}{Stability at water hardness of 34 ppm} |
| after 0.5 h | + | + | + | + | + | + |
| after 1 h | + | + | + | + | + | + |

TABLE 2-continued

| Emulsion stability (all amounts in % b.w.) | | | | | | |
|---|---|---|---|---|---|---|
| after 4 h | # | + | + | # | # | # |
| after 24 h | # | # | + | − | − | − |
| Stability at water hardness of 342 ppm | | | | | | |
| after 0.5 h | + | + | + | + | + | + |
| after 1 h | + | + | + | # | # | + |
| after 4 h | # | # | + | # | # | # |
| after 24 h | # | # | + | − | − | − |
| Stability at water hardness of 1000 ppm | | | | | | |
| after 0.5 h | + | + | + | + | + | + |
| after 1 h | # | # | + | # | # | # |
| after 4 h | # | # | + | − | − | − |
| after 24 h | # | # | + | − | − | − |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed. Thus, it is intended that the present invention include modifications and variations that are within the scope of the appended claims and their equivalents.

What is claimed is:

1. A biocide composition, comprising
   (a) about 0.1 to about 5% b.w. a herbicide;
   (b) about 50 to about 90% b.w. a fatty acid amide;
   (c) about 5 to about 15% b.w. a fatty acid; and optionally
   (d) about 0.5 to about 5% b.w. an emulsifier and/or
   (e) about 0.1 to about 1% b.w. a polyol
   with the proviso that the amounts add to 100%, wherein said herbicide exhibits solubility in water of less than 5 g/l at a temperature of 20° C. and a water hardness of at most 1000 ppm, and wherein said biocide composition is free of naphthalene.

2. The biocide composition according to claim 1, wherein said herbicide is a solid.

3. The biocide composition according to claim 1, wherein said herbicide is pyraflufen-ethyl.

4. The biocide composition according to claim 1, wherein said fatty acid amide is according to general formula (I)

$$R^1CONR^2R^3 \quad (I)$$

wherein $R^1CO$ represents a linear or branched, saturated or unsaturated, optionally hydroxyl-substituted acyl radical having 2 to 22 carbon atoms and 0 or 1 to 3 double bonds, and $R^2$ and $R^3$ independently represent either hydrogen or alkyl radicals having 1 to 12 carbon atoms.

5. The biocide composition according to claim 1, wherein said fatty acid amide is derived from a fatty acid having 6 to 10 carbon atoms or lactic acid.

6. The biocide composition according to claim 1, wherein said fatty acid amide is a fatty acid dialkyl amide.

7. The biocide composition according to claim 1, wherein said fatty acid amide is a fatty acid dimethyl amide.

8. The biocide compositions according to any claim 1, wherein said fatty acid amide is a $C_6$-$C_{10}$ fatty acid dimethyl amide.

9. The biocide composition according to claim 1, wherein said fatty acid is according to general formula (II)

$$R^2CO\!-\!OH \quad (II)$$

wherein $R^2CO$ represents a linear or branched, saturated or unsaturated, optionally hydroxyl-substituted acyl radical having 6 to 22 carbon atoms and 0 or 1 to 3 double bonds.

10. The biocide compositions according to claim 1, wherein said fatty acid is a $C_{16}$-$C_{18}$ fatty acid having 0 or 1 to 3 double bonds.

11. The biocide composition according to claim 1, wherein said fatty acid is tall oil fatty acid.

12. The biocide composition according to claim 1, wherein said emulsifier is a non-ionic emulsifier.

13. The biocide compositions according to claim 1, wherein said emulsifier is a polymeric non-ionic emulsifier.

14. The biocide composition according to claim 1, wherein said emulsifier is the alkoxylation product of an alkyl phenol.

15. The biocide composition according to claim 1, wherein said emulsifier is a nonyl phenol EO/PO block copolymer.

16. The biocide compositions according to claim 1, wherein said polyol is selected from the group consisting of glycerol, alkylene glycols, technical oligoglycerol mixtures with a degree of self-condensation of 1.5 to 10, methylol compounds, lower alkyl glucosides, sugar alcohols containing 5 to 12 carbon atoms, sugars containing 5 to 12 carbon atoms, and amino sugars.

17. The biocide composition according to claim 1, wherein the biocide composition comprises:
   (a) a solid herbicide;
   (b) a fatty acid amide derived from a $C_6$-$C_{10}$ fatty acid or lactic acid;
   (c) a $C_{16}$-$C_{18}$ fatty acid; and optionally
   (d) a non-ionic emulsifier and/or
   (e) a polyol.

18. The biocide composition according to claim 1, wherein the composition in the absence of dilution by water comprises about 0.1 to about 5% b.w. a herbicide.

19. A biocide composition comprising
   (a) about 0.1 to about 5% b.w. pyraflufen-ethyl;
   (b) about 50 to about 90% b.w. a $C_6$-$C_{10}$ fatty acid dimethyl amide;
   (c) about 5 to about 15% b.w. tall oil fatty acid; and optionally
   (d) about 0.5 to about 5% b.w. nonyl phenol EO/PO block copolymer and/or
   (e) about 0.1 to about 1% b.w. propylene glycol
   with the proviso that the amounts add to 100%,
   wherein said herbicide exhibits solubility in water of less than 5 g/l at a temperature of 20° C. and a water hardness of at most 1000 ppm.

20. A method of controlling weeds, the method comprising using the composition of claim 1 as a weed control agent.

21. A method of protecting crops, the method comprising using the composition of claim 1 as a crop protection agent.

22. A process for controlling and fighting weed growth in a crop field, wherein a composition according to claim 1 is diluted with water to provide a sprayable emulsion or dispersion and said emulsion or dispersion is applied to the crop.

23. The process according to claim 22, wherein the emulsion or dispersion is in the form of a tank mix having a water content of 50 to 95% b.w.

* * * * *